(12) United States Patent
Kohlrausch et al.

(10) Patent No.: US 8,141,401 B2
(45) Date of Patent: Mar. 27, 2012

(54) METHOD AND APPARATUS FOR ANALYZING A LAYER OF METAL-WORKING LIQUID

(75) Inventors: Arnt Kohlrausch, Kreuztal (DE); Hartmut Pawelski, Ratingen (DE); Hans-Peter Richter, Friedewald (DE)

(73) Assignee: SMS Demag Aktiengesellschaft, Duesseldorf (DE)

( * ) Notice: Subject to any disclaimer, the term of this patent is extended or adjusted under 35 U.S.C. 154(b) by 681 days.

(21) Appl. No.: 12/304,274

(22) PCT Filed: Jun. 8, 2007

(86) PCT No.: PCT/EP2007/005076
§ 371 (c)(1),
(2), (4) Date: Dec. 11, 2008

(87) PCT Pub. No.: WO2007/147489
PCT Pub. Date: Dec. 27, 2007

(65) Prior Publication Data
US 2009/0201492 A1    Aug. 13, 2009

(30) Foreign Application Priority Data

Jun. 17, 2006  (DE) .................... 10 2006 027 972
Dec. 6, 2006   (DE) .................... 10 2006 057 476

(51) Int. Cl.
*G01N 21/27*   (2006.01)
*B21B 37/18*   (2006.01)

(52) U.S. Cl. .................. 72/42; 72/8.3; 436/60; 436/164

(58) Field of Classification Search ........... 72/9.1, 72/9.2, 9.4, 11.1, 11.8, 41, 42, 43, 44, 240; 436/60, 164
See application file for complete search history.

(56) References Cited

U.S. PATENT DOCUMENTS

| 3,954,119 | A | * | 5/1976 | Kunioka et al. | 72/236 |
| 4,024,742 | A | * | 5/1977 | Vucich et al. | 72/42 |
| 4,882,490 | A | | 11/1989 | Takaaki et al. | |
| 5,224,051 | A | * | 6/1993 | Johnson | 72/42 |
| 5,838,561 | A | | 11/1998 | Owen | |
| 5,919,707 | A | | 7/1999 | Banks et al. | |
| 6,089,069 | A | | 7/2000 | Seidel | 72/236 |
| 6,412,642 | B2 | | 7/2002 | Charles et al. | |
| 7,185,520 | B2 | * | 3/2007 | Pampel et al. | 72/11.8 |
| 2002/0019321 | A1 | * | 2/2002 | Balliett | 508/246 |

FOREIGN PATENT DOCUMENTS

| CA | 2618836 | | 3/2007 |
| DE | 102005042020 | | 3/2007 |
| GB | 1191476 | * | 5/1970 |
| JP | 61199507 A | | 9/1986 |
| JP | 07016630 A | | 1/1995 |
| JP | 07243970 A | | 9/1995 |
| JP | 09113231 A | | 5/1997 |
| JP | 2002143904 A | | 5/2002 |
| JP | 03252512 A | | 11/2011 |
| WO | WO 99/15881 | * | 4/1999 |

* cited by examiner

*Primary Examiner* — David Jones
(74) *Attorney, Agent, or Firm* — Andrew Wilford

(57) ABSTRACT

In a shaping process a metal strip is passed in a rolling direction through shaping rolls and a layer of treatment liquid is applied to a surface of the strip upstream of the shaping rolls. Measurement variables of the liquid on the surface are analyzed by laser-induced, time resolved fluorescent spectroscopic analysis or spectroscopic analysis in the infrared band.

13 Claims, 2 Drawing Sheets

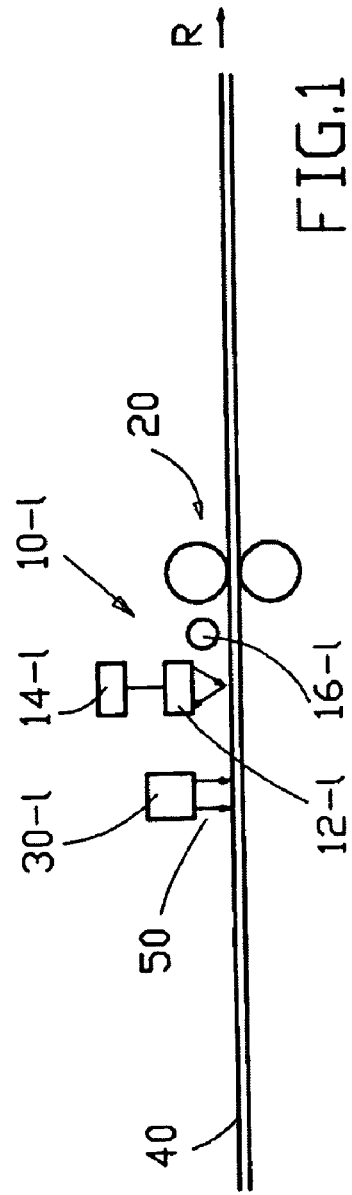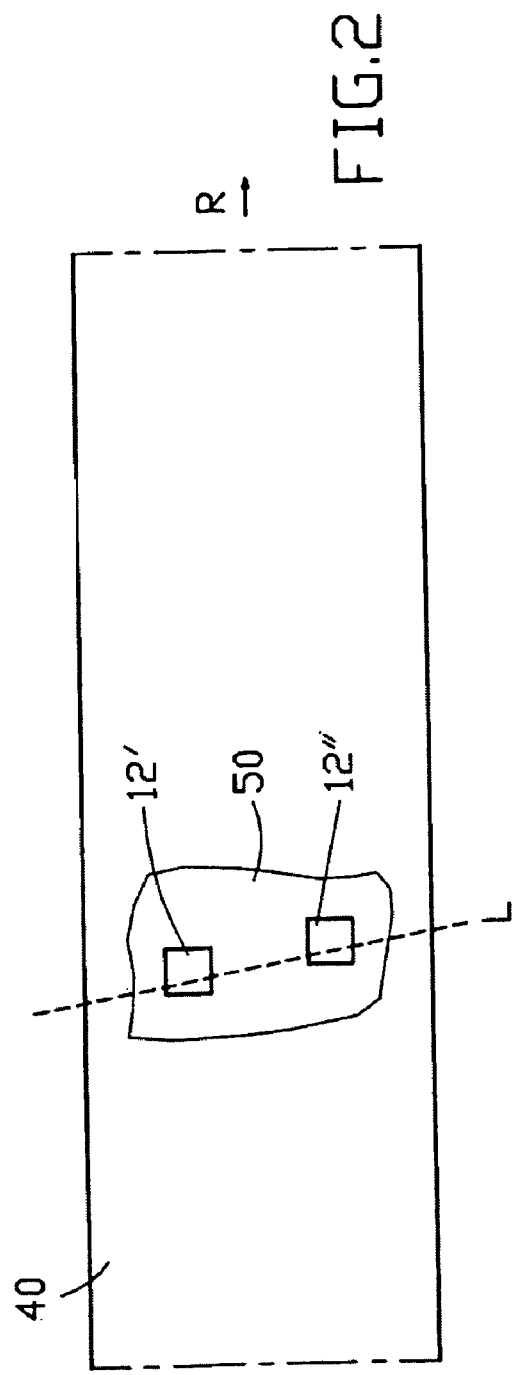

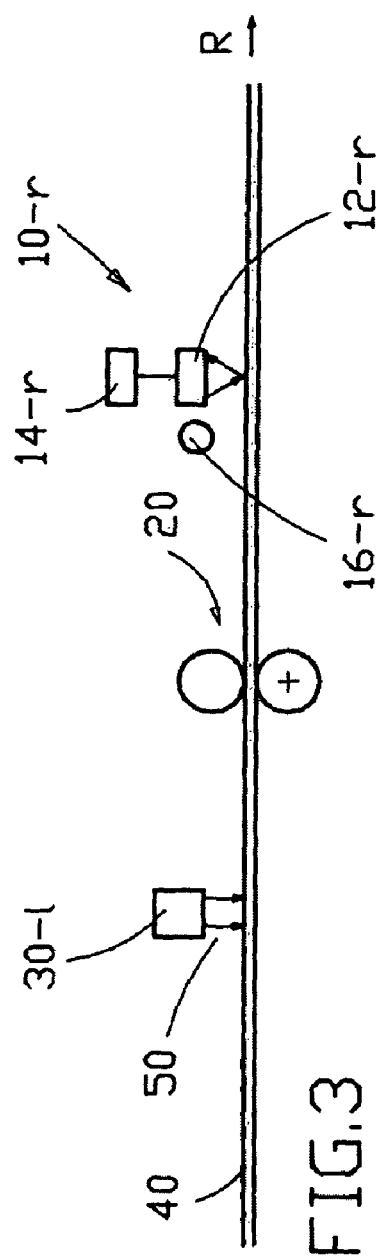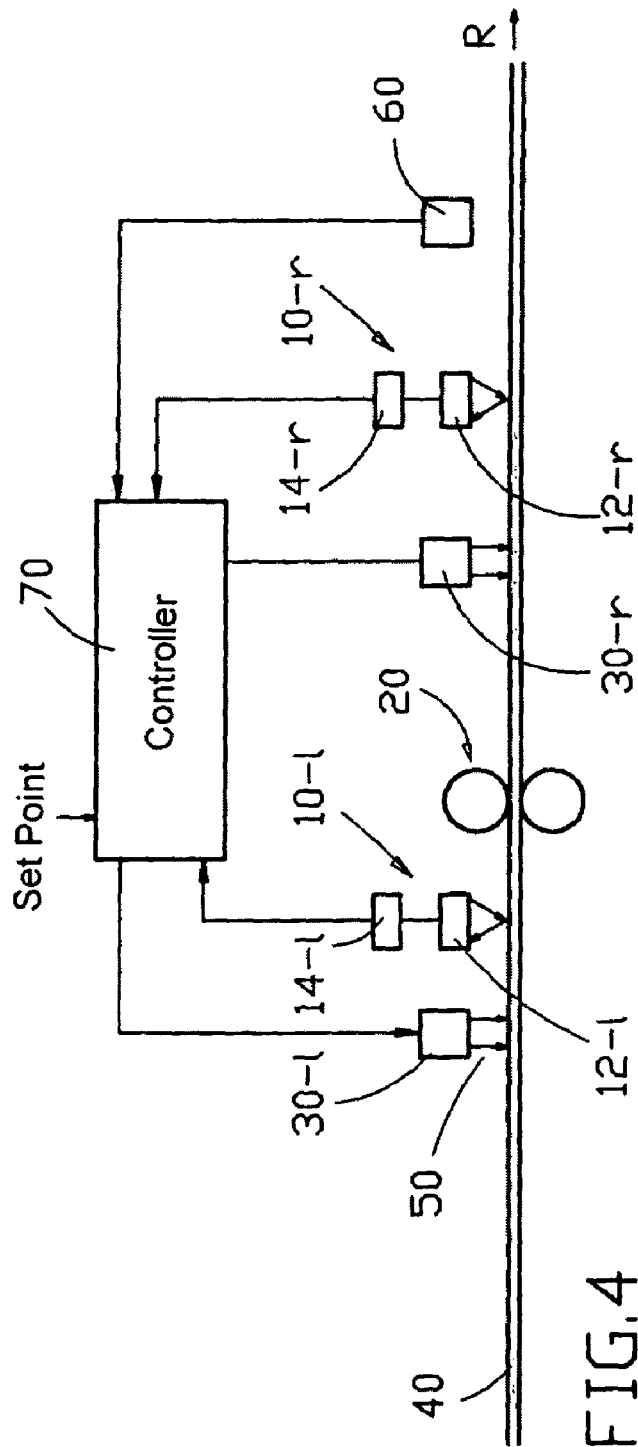

METHOD AND APPARATUS FOR ANALYZING A LAYER OF METAL-WORKING LIQUID

CROSS REFERENCE TO RELATED APPLICATIONS

This application is the US-national stage of PCT application PCT/EP2007/005076 filed 8 Jun. 2007, published 27 Dec. 2007 as WO2007/147489, and claiming the priority of German patent application 102006027972.7 itself filed 17 Jun. 2006 and PCT patent application PCT/EP2007/005076 itself filed 8 Jun. 2007, whose entire disclosures are herewith incorporated by reference.

BACKGROUND OF THE INVENTION

The invention relates to a method of analyzing a layer of a treatment liquid on the surface of a workpiece to be shaped, particularly a metal strip, upstream and/or downstream of the shaping process, especially a roll process, for various measuring variables. The invention also concerns an apparatus with at least one detector for generating scanning signals of a layer of the treatment liquid on the surface of the workpiece to be shaped, the detector being located upstream and/or downstream of a shaping device, particularly a roll stand, and with an evaluator for analyzing the scanning signal generated by the detector for various specific measurement variables of the treatment liquid.

BACKGROUND OF THE INVENTION

In principle, in shaping processes, there is a need for the use of a treatment liquid for sufficient separation of the rolling stock and the rolls. Should this separation not be successful in the desired manner, metallic contact occurs between the parts that are undergoing shaping, and based on their relative displacement to one another, faults result in the desired surface structure of the rolling stock.

Concerning this, several methods of the generic type are known in prior art.

From DE 197 44 503 [U.S. Pat. No. 6,089,069], an apparatus and a method are known for influencing frictional relationships between the upper and lower roll in roll stands of warm broad strip or cold-strip conveyor lines. This way, the method is essentially characterized in that the upper face of the strip and/or the lower face of the strip of the rolling stock is wetted at the intake side of the roll stand by a sprayer with a defined quantity of fluid, and a controller regulates the quantity specifications and discharge of the fluid, a predetermined control variable or is calculated amount being used in connection with the actual roll torque of the lower and/or upper roll. A method of this type ensures in particular that between the upper face of the strip of the rolling stock and the upper roll, as well as also between the lower face of the strip of the rolling stock and the lower roll nearly identical frictional relationships are created in order to improve the degree of effectiveness of the rolling process as well as to reduce wear of the upper and lower rolls and to continue dampening the frequently occurring tendency of vibration at larger reductions of thickness.

In this and other known methods there exists a basic need to achieve greater production of high-quality metallic rolling strip by saving steps in the process, so that better strip quality can be achieved in a more stable rolling process, particularly by adjusting the friction in the roll gap. Concerning this, German patent application DE 10 2005 042 020.6 [CA 2,618,836], which has older priority, belongs to the applicant and was not published, suggests that on the intake side a minimum quantity of pure lubricant without high water content with controlled viscosity depending on a number of process data elements be applied continually dosed online via a physical computer model.

This results in a more stable roll process, in particular, an adjustment of the friction is made possible in the roll gap. Beyond that, it is advantageous that a subsequent removal of residual oil is no longer required and thereby, additional process steps are saved, because minimal lubrication means that only as much lubricant is applied at the intake side as is necessary for achieving the desired product quality and as is also actually consumed during the rolling process. Moreover, devices for oil emulsions and related expenses for such, as well as their disposals are eliminated.

OBJECT OF THE INVENTION

Based on that, the invention is based on the problem that the method that is known from the German patent application (File number: DE 10 2005 042 020.6 [CA 2,618,836]) that has not undergone prior publication, as well as a corresponding apparatus for executing this method be developed further in such a way that a specific and suitable measuring method and an apparatus for the evaluation of the treatment liquid is made available on the workpiece to be shaped, while retaining the previous advantages.

SUMMARY OF THE INVENTION

Concerning the method, this problem is solved according to the invention in that the analysis of the treatment liquid takes place online with the aid of a spectroscopic analysis. The problem with respect to the apparatus is solved according to the invention by designing the evaluator as an online spectroscopic evaluator.

Within the framework of the description at hand, the term treatment liquid describes a general substance that serves to ensure sufficient separation between the workpiece to be shaped and the shaping apparatus, particularly working rolls in a shaping process, particularly a roll process.

The invention include three different alternatives for the analysis of the treatment liquid on the workpiece to be shaped, namely an analysis before the shaping process, an analysis after the shaping process and an analysis before and after the shaping process.

The analysis of the treatment liquid on the workpiece to be shaped that takes place before entering the shaping process advantageously makes control of the quality of the application of the metal working product possible, for example, in the sense of, whether the application has taken place homogeneously or—perhaps targeted—non-homogeneously.

Simply by analyzing the residual quantity of the treatment liquid that remains on the surface of the rolling stock after the shaping process it can advantageously be determined whether this residual quantity is too large, too small or acceptable; accordingly, the quantity of treatment liquid that is applied to the workpiece to be shaped before the shaping process can be decreased or increased or can remain unchanged. The result of the analysis with respect to the chemical composition of the treatment liquid on the workpiece to be shaped after the shaping process can advantageously be used for targeted adjustments—before the shaping process—of the composition of the treatment liquid and/or its temperature when it is applied to the workpiece to be shaped.

The mentioned third alternative, namely an analysis of the treatment liquid before and after the shaping process advantageously makes drawing a conclusion about the consumption of treatment liquid during the shaping process possible. The quantity consumed of the treatment liquid determined in this way in turn makes it possible to draw a conclusion about the thermal conditions during the shaping process. In addition to the quantity consumed, the analysis that is done with the aid of a spectroscopic analysis also makes a comparison of the chemical composition of the treatment liquid before and after the shaping process possible, the comparison being the basis for a conclusion concerning the consumption of certain components of the treatment liquid, such as, for example, additives or the formation of reactants during the shaping process. Such evidence having been determined can be supported in a targeted manner if desired, i.e. in those cases in which the substances relevant for shaping are only formed during the shaping process, or they can be counteracted at an early stage.

Finally, it is to be mentioned that the spectroscopic analysis of the treatment liquid takes place online. The results of the spectroscopic analysis of the treatment liquid are thus available in real time and can be used directly, i.e. even while the shaping process is running in order to influence it. This influencing can take place in the form of a targeted control or a feedback-controlled influence of the shaping apparatus, or, as has been mentioned already, the treatment liquid that has been applied.

A preferred embodiment of the present invention concerns the spectroscopic analysis of laser-induced, time-induced fluorescent spectroscopic analysis or a spectroscopic analysis in the infrared band. These are particularly suitable measurement methods for analyzing a layer of treatment liquid.

According to a further characteristic of an embodiment of the present invention, it is provided that the treatment liquid is, for example, a lubricant, a cooling lubricant, a tempering agent or a wet tempering agent.

It is logical according to a further characteristic of an embodiment of the present invention that the analyzed measurement variables of the treatment liquid are, for example, its quantity per surface unit, its composition, and the homogeneity of its distribution on the workpiece to be shaped and/or its layer thickness. Concerning the advantages that result thereby, reference is made to the explanations that have already been made.

According to a further embodiment of the present invention it is recommended that the measurement variables are inputted to at least one control loop as control variables which initiates an application of the treatment liquid onto the workpiece to be shaped according to the specifications of predetermined set points, the set point values for the control variables being specified in such a way that they lead to—based on the previously known shaping process—setting certain shaping parameters for the shaping process itself and/or for forming quality characteristics to the respectively desired degree in the shaped product. The shaping parameters that can be influenced can be, in a preferred embodiment for example, the level of the roll-spreading force or the strength of the vibrations of rolls in a shaping device.

According to a further characteristic of the present invention it is provided that the control loop—in the event an undesired or erroneous, for example, contaminated composition of the treatment liquid is captured—is designed such that it is able—according to specified set points for the composition of the treatment liquid—to subsequently mix into or correct the treatment liquid even while the shaping process is running by use of supplies of various components from which the treatment liquid is made.

It is logical, according to a further characteristic of the present invention that for the calculation of the set points, the shaping process be simulated by a mathematical model.

According to a further characteristic of the present invention it is provided that the quality characteristics for the workpiece to be shaped are, for example, its flatness, its shine or its texture, particularly the absence of fishbone patterns.

According to an additional characteristic concerning the method of the present invention, individual components of the treatment liquid, markers or tracer substances are added. These marker and/or tracer substances can, if desired, be added to the individual components of the treatment liquid in order to adjust their signal strength in suitable manner.

In the preferred embodiment form of the present invention with respect to the apparatus, at least one irradiation means for irradiating the treatment liquid on the workpiece to be shaped while it is being scanned is provided. The irradiation activates or strengthens the effect of the marker and/or tracer substances and generally improves the detection and thereby the result of the spectroscopic analysis, for example, the quantity distribution or the distribution of the composition of the treatment liquid, even transversely of the roll direction.

If the scanners or the irradiation source are only upstream and/or downstream of the roll device and in comparison to the width of the workpiece to be shaped of small dimension, it is advantageous if they are made to be moveable transversely of the roll direction in order to make an analysis of the treatment liquid possible that covers the entire width of the workpiece to be shaped. If the detector is designed in the form of a number of irradiation elements upstream of and/or downstream of the roll gap, these elements are not required to be displaceable; however, it would be advantageous if these elements were also located in a direction transversely of the roll direction above the workpiece to be shaped in order to make analysis of the treatment liquid covering the entire width of the workpiece to be shaped possible. The detector or the detection elements are preferably designed as scanners.

Finally, according to a last characteristic of the present invention, the evaluator is designed for executing the method according to the invention.

BRIEF DESCRIPTION OF THE DRAWING

Four figures are enclosed with the description, in which:

FIG. 1 shows a first example of an embodiment of the invention;

FIG. 2 shows a variation of the design of the detector;

FIG. 3 shows a second example of an embodiment of the invention; and

FIG. 4 shows a third example of an embodiment of the invention.

DETAILED DESCRIPTION

In the following, the invention will be described in detail in the form of examples by referring to the figures that were mentioned. In all figures, identical technical elements are identified with the same reference numbers. The addition "l" or "r" to individual reference numbers signifies that the correspondingly identified elements as seen in a roll direction R are located either upstream of (−l) or downstream of (−r) the roll device 20. To keep it simple, the reference numbers in the following description are used without these additions, as a rule, to the extent this does not appear to be absolutely required for showing a specific situation.

In general, the invention concerns a method and a corresponding apparatus for analyzing a layer of a treatment liquid on the surface of a workpiece to be shaped, which is fed into a shaping process.

Concerning this, FIG. 1 shows a first example. Specifically, FIG. 1 is a metal-shaping device 20 in the form of a rolling plant that is shown schematically. A workpiece 40 to be shaped is fed into the metal-shaping device 20 for shaping, for example, for the purpose of thickness reduction. The workpiece 40 to be shaped runs through the metal-shaping device 20 in the roll direction R.

For simplification of the shaping process and to improve the quality of the workpiece 40 to be shaped after the shaping process with respect to certain quality characteristics, such as, for example, flatness, shine, texture or the absence of fishbone patterns, etc., a treatment liquid 50 is applied to the workpiece to be shaped with the aid of a row of spray nozzles 30 before it is fed into the metal-shaping device 20. The treatment liquid can be, for example, a lubricant, cooling lubricant, a tempering agent or a wet tempering agent. As FIG. 1 shows, the treatment liquid can be applied to the upper surface of the workpiece 40 to be shaped or on its underside (not shown, this also applies to all other examples of embodiments that follow).

In the first embodiment of the invention shown in FIG. 1, the treatment liquid that is applied to the surface of the workpiece 40 to be shaped is analyzed with the aid of an apparatus 10 according to the invention before it enters the metal-shaping device 20 together with the workpiece to be shaped. The apparatus in accordance with the invention comprises a detector 12 for generating a scan signal from a layer of the treatment liquid 50 on the surface of the workpiece 40 to be shaped; the detector 12 can be a scanner, for example.

FIG. 2 shows an example of an embodiment for the spatial design of a detector 12. It is shown there by way of example that the detector can consist of individual detection elements 12', 12'' . . . , preferably scanner elements, that are fixed along a line L with one component transversely of roll direction R. Alternative to that, detector 12 can also only consist of a scanner element, which then, however, is preferably moveable with one component transversely of the roll direction R and thus across the width of the workpiece to be shaped. Both alternative designs serve to determine, for example, the quantities or the temperature distribution of the treatment liquid or the distribution of its chemical composition even transversely of the roll direction R.

It can further be seen in FIG. 1, that the scan signal generated by the detector 12 is inputted to an evaluator 14 in order to be evaluated by it. The evaluator is a device for spectroscopic analysis, that, for example, works in the infrared band or according to the principle of laser-induced time-induced fluorescent spectroscopic analysis. The evaluator 14 analyzes the scanning signal it receives from the detector 12 to determine various measurement variables of the treatment liquid 50. These analyzed measurement variables can be, for example, the quantity of the treatment liquid per unit of surface area, its chemical composition, the homogeneity of its distribution on the workpiece 40 to be shaped, for example, even transversely of the roll direction R and/or the thickness of the layer of treatment liquid 50 on the workpiece 40 to be shaped.

The analysis of the treatment liquid 50 according to the embodiment shown in FIG. 1 before its entry into the metal-shaping device 20 with the aid of the detector described above with reference to FIG. 2 preferably makes, for example, it possible to determine whether the treatment liquid has been applied in the direction of width, i.e. transversely of roll direction R onto the surface of the workpiece 40 to be shaped in the desired manner. As a rule, an even homogeneous distribution is desired; alternatively, a targeted non-homogeneous distribution may be desired as well. The distribution relates particularly to the thickness of the layer of the applied treatment liquid 50; but it can also be related to its local composition. Should the spectroscopic analysis performed by the evaluator 14 result in a distribution that deviates from the desired quantity distribution, then the location shown in FIG. 1 makes it possible to initiate a targeted effect on the row of spray nozzles 30, by, for example turning individual spray nozzles on or off in a targeted manner. If required, the chemical composition of the applied treatment liquid can perhaps also be influenced in a corrective manner by increasing or decreasing the amount of the components of this treatment liquid by using respective supplies and custom mixing the treatment liquid. Based on the fact that the spectroscopic analysis of the scan signal takes place online in accordance with the invention, the corrective measures that have been described by way of example can be made in real time, so to speak, even while a shaping process is running.

During the scanning process, the treatment liquid 50 is irradiated on the surface of the workpiece 40 to be shaped, preferably with an irradiation means 16, in order to improve recognition of the measurement variables of the treatment liquid by the detector.

FIG. 3 shows a second example of an embodiment of the present invention, the apparatus 10 in accordance with the invention seen in the roll direction R being only downstream of the shaping device 20. There, the apparatus 10 makes it possible to perform an analysis of the treatment liquid 50 on the surface of the workpiece 40 to be shaped after the shaping process has taken place. Thus the possibility exists of in particular determining the residual quantity of treatment liquid 50 that remains on the surface after the shaping process. Preferably, the residual quantity can, for example, be inputted to a feedback-type controller of the quantity of treatment liquid 50 that regulates the quantity of treatment liquid fed to the shaping device, for example, a minimum quantity of lubricant that is fed into the shaping device. The minimum quantity of lubricant is distinguished in that at the input side of shaping device 20, only as much treatment liquid 50 is applied as is needed during the shaping process. Of course, the analysis of the treatment liquid 50 downstream of shaping device 20 in turn makes analysis of the chemical composition of treatment liquid 50 and if needed, required corrections of the chemical composition possible. As has already been mentioned above in reference to FIG. 1, the chemical composition can be controlled in a targeted manner by targeted influence on quantities of components of the treatment liquid by access us of respective supplies. Even eventual contamination in the treatment liquid can be recognized in a timely manner and perhaps eliminated. Contamination of treatment liquid 50 can take place, for example, by hydraulic fluid mixing with the treatment liquid 50 during the shaping process in the shaping device 20.

Moreover, as a result of the information about the chemical composition of the residual quantity of the treatment liquid on the surface of the workpiece 40 to be shaped after the shaping process, the temperature of the treatment liquid can be addressed in a targeted manner.

Finally, FIG. 4 shows a third example of an embodiment of the present invention, essentially showing a combination of the first and second embodiments. The combination is that in the third embodiment the apparatus 10 according to the invention is located upstream as well as downstream of the shaping device 20. As a result of the location of the apparatus on both sides it becomes possible to determine the measurement variables for the treatment liquid 50 that are mentioned above before the shaping process, as well as to compare them afterward. Thus, for example, from the detected quantity of the treatment liquid 50 upstream and downstream of the shaping device 20, conclusions can be drawn about the consumption of treatment liquid during the shaping process. The consumption in turn makes a conclusion concerning the thermal conditions during the shaping process possible and the thermal conditions in turn—when the shaping process is known precisely—a conclusion about the quality of the workpiece to be shaped after running through the shaping process, i.e. a conclusion about its shine, flatness, texture or its depth of roughness.

A comparison of the chemical composition of the treatment liquid 50 upstream of and downstream of the shaping device 20 makes it possible to draw a conclusion about the consumption of certain additives or the formation of reactants during the shaping process. This behavior can be counteracted or it can be amplified in a targeted manner, the latter in cases where substances relevant for shaping are formed only during the shaping process.

For the execution of the comparison described just now and for the execution of suitable influences on the treatment liquid 50 or the shaping process, a comparator or controller is required that is identified in FIG. 4 at reference 70.

In particular, the controller 70 can be designed to is suitably regulate the entire shaping process based on mathematical models that which can be set with reference to the above mentioned quality characteristics that are defined beforehand for the workpiece 40 to be shaped. To get these quality characteristics, the controller 70 is fed suitable measurement variables that represent actual values and that are typically compared with set-point values.

Thus, the measurement variables that have been determined by a reporting device 14 in accordance with the invention and defined above, such as, for example, the quantity of the treatment liquid 50 per surface unit, its temperature, its chemical composition or its distribution on the surface of the workpiece to be shaped are inputted into the controller 70 and evaluated relative to a mathematical model of the shaping process. For example, a measuring apparatus 60 in FIG. 4 measures the remaining measurement variables as initial measurement variables for controller 70, which are not made available by the evaluator 14. For developing the desired quality characteristics of the workpiece to be shaped, the controller 70 is designed to influence the shaping process as desired after analyzing the measurement variables it has received by using the mathematical model. Traditionally, this influence takes place particularly as a result of setting the roll-spreading force of the shaping device 20, but it can also influence—in accordance with the present invention and as described above by reference to the examples of embodiments that have already been described—the quantity, the chemical composition, the distribution or the temperature of applied treatment liquid 50.

The invention claimed is:

1. In a shaping process where a metal strip is passed in a rolling direction through shaping rolls and a layer of treatment liquid is applied to a surface of the strip upstream of the shaping rolls, the improvement comprising the step of:
analyzing measurement variables of the liquid on the surface by laser-induced, time resolved fluorescent spectroscopic analysis or spectroscopic analysis in the infrared band.

2. The method according to claim 1, wherein the treatment liquid is a lubricating agent, a cooling lubricant, a tempering agent or a wet tempering agent.

3. The method according to claim 1, wherein the measurement variables of the treatment liquid are quantity per surface unit, temperature, composition, homogeneity of distribution on the workpiece to be shaped, or thickness of the layer.

4. The method according to claim 3, further comprising the steps of:
inputting the measurement variables as control variables into at least one control loop;
initiating with the control loop an application of the treatment liquid to the workpiece to be shaped according to a specification of predetermined set points establish predetermined shaping parameters in the shaping process itself or create predetermined quality characteristics in a resultant shaped product.

5. The method according to claim 4 wherein the shaping parameters that can be influenced are the size of a roll-spreading force or the strength of vibration of the rolls.

6. The method according to claim 4, further comprising the step, when the control loop detects undesired, faulty, or contaminated composition of the treatment liquid, the method further comprising the step of:
adding components that comprise the treatment liquid by using supplies of the components and subsequently mixing them according to predetermined set points into the treatment liquid.

7. The method according to claim 4, wherein, for calculating the set points, the shaping process is simulated by a mathematical model.

8. The method according to claim 4, wherein the quality characteristics for the shaped workpiece to be shaped are flatness, shine, or texture.

9. The method according to claim 1, further comprising the step of:
adding markers or tracer substances in targeted manner to individual components of the treatment liquid.

10. In an apparatus where a metal strip is passed in a rolling direction through shaping rolls of a roll stand and a layer of treatment liquid is applied to a surface of the strip upstream of the shaping rolls, the improvement comprising
at least one detector for generating a scanning signal of a layer of treatment liquid on the surface of the strip, the detector being being spaced in the direction from roll stand; and
an evaluator for analyzing the scan signal generated by detector for various specific measurement variables of the treatment liquid; wherein the evaluator carries out online spectroscopic analysis by laser-induced, time resolved fluorescent spectroscopic analysis or spectroscopic analysis in the infrared band.

11. The apparatus according to claim 10, further comprising:
at least one irradiation means for irradiating the treatment liquid on the workpiece to be shaped during scanning.

12. The apparatus according to claim 10, further comprising:
a detector with a number of detector elements located on a line that runs in one direction with one component transversely of the roll direction on the workpiece to be shaped.

13. The apparatus according to claim 10, wherein the detector is a scanner.

* * * * *